United States Patent [19]

Koerber et al.

[11] Patent Number: 5,371,070
[45] Date of Patent: Dec. 6, 1994

[54] BICYCLIC GNRH ANTAGONISTS AND A METHOD FOR REGULATING THE SECRETION OF GONADOTROPINS

[75] Inventors: Steven C. Koerber, Encinitas; John S. Porter, Leucadia; Jean E. F. Rivier, La Jolla, all of Calif.

[73] Assignee: The Salk Institute for Biological Studies, San Diego, Calif.

[21] Appl. No.: 973,989

[22] Filed: Nov. 9, 1992

[51] Int. Cl.$^5$ .......................... C07K 7/06; C07K 5/12; A61K 37/38

[52] U.S. Cl. .......................... 514/9; 530/317; 530/313; 530/328; 514/11; 514/15

[58] Field of Search .......................... 530/317, 313, 328; 514/9, 11, 15

[56] References Cited

U.S. PATENT DOCUMENTS

| | | | |
|---|---|---|---|
| 4,133,805 | 1/1979 | Yardley | 260/112.5 |
| 5,043,322 | 8/1991 | Rivier et al. | 514/12 |
| 5,064,939 | 11/1991 | Rivier et al. | 530/317 |

OTHER PUBLICATIONS

Theobald, et al., "Novel Gonadotropin-Releasing Hormone Antagonists: Peptides Incorporating Modified $N^{107}$-Cyanoguanidino Moieties", *J. of Medicinal Chemistry*, 34, 2395–2402 (1991).

*Primary Examiner*—Robert J. Hill, Jr.
*Assistant Examiner*—Carol A. Salata
*Attorney, Agent, or Firm*—Fitch, Even, Tabin & Flannery

[57] ABSTRACT

Peptides which have substantial bioactivity to inhibit the secretion of gonadotropins by the pituitary gland and to inhibit the release of steroids by the gonads. Administration of an effective amount of such GnRH antagonists prevents ovulation and/or the release of steroids by the gonads. They may also be used to treat steroid-dependent tumors, such as prostatic and mammary tumors. The peptides are bicyclic analogs of the decapeptide GnRH having two covalent bonds, between the residues in the 4- and 10-positions and the residues in the 5- and 8-positions. The latter linkage includes peptide bonds between a residue of an α-amino acid outside of the main chain and a side-chain carboxyl group of the 5-position residue and a side-chain amino group of the 8-position residue.

9 Claims, No Drawings

BICYCLIC GNRH ANTAGONISTS AND A METHOD FOR REGULATING THE SECRETION OF GONADOTROPINS

This invention was made with Government support under grant number HD-13527 and contracts NO1-HD-1-3100 and NO1-HD-0-2906 awarded by the National Institutes of Health. The Government has certain rights in this invention.

The present invention relates to synthetic peptides containing D-isomers which have biological properties antagonistic to GnRH and which inhibit the release of gonadotropins by the pituitary gland in mammalians, including humans. It also relates to methods of preventing ovulation and/or inhibiting the release of steroids. More particularly, the present invention is directed to peptides which inhibit gonadal function and the release of the steroidal hormones, progesterone and testosterone.

BACKGROUND OF THE INVENTION

The pituitary gland is attached by a stalk to the region in the base of the brain known as the hypothalamus. In particular, follicle stimulating hormone (FSH) and luteinizing hormone (LH), sometimes referred to as gonadotropins or gonadotropic hormones, are released by the pituitary gland. These hormones, in combination, regulate the functioning of the gonads to produce testosterone in the testes and progesterone and estrogen in the ovaries, and they also regulate the production and maturation of gametes.

The release of a hormone by the anterior lobe of the pituitary gland usually requires a prior release of another class of hormones produced by the hypothalamus. One of the hypothalamic hormones acts as a factor that triggers the release of the gonadotropic hormones, particularly LH, and this hormone is referred to herein as GnRH although it has also been referred to as LH—RH and as LRF. GnRH was isolated and characterized as a decapeptide some 20 years ago, and it was found that analogs of GnRH having a D-isomer instead of Gly in the 6-position, such as [D—Ala$^6$]—GnRH (U.S. Pat. No. 4,072,668) having the following formula:

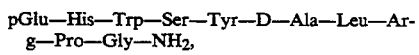

pGlu—His—Trp—Ser—Tyr—D—Ala—Leu—Arg—Pro—Gly—NH$_2$, have greater binding strength to the receptor and greater biological potency than the native hormone.

Peptides are compounds which contain two or more amino acids in which the carboxyl group of one acid is linked to the amino group of an adjacent acid. The formula for the GnRH analog as represented above is in accordance with conventional representation of peptides where the amino terminus appears to the left and the carboxyl terminus to the right. The position of a particular amino acid residue is identified by numbering the amino acid residues from left to right. In the case of GnRH, the hydroxyl portion of the carboxyl group of glycine at the C-terminus has been replaced with an amino group(NH$_2$), i.e. the C-terminus has been amidated.

The abbreviations for the common individual amino acid residues are conventional and are based on the trivial name of the amino acid, e.g. pGlu is pyroglutamic acid, Glu is glutamic acid, His is histidine, Trp is tryptophan, Ser is serine, Tyr is tyrosine, Gly is glycine, Leu is leucine, Nle is norleucine, Orn is ornithine, Arg is arginine, Har is homoarginine, Pro is proline, Sar is sarcosine, Phe is phenylalanine, Ala is alanine, Val is valine, Nva is norvaline, Ile is isoleucine, Thr is threonine, Lys is lysine, Asp is aspattic acid, Ash is asparagine, Gln is glutamine, Cys is cysteine, and Met is methionine. Except for glycine, the amino acids which appear in the peptides of the invention are of the L-configuration unless noted otherwise.

There are reasons for desiring to prevent ovulation in female mammalians, and the administration of GnRH analogs that are antagonistic to the normal function of GnRH have been used to suppress or delay ovulation. For this reason, analogs of GnRH containing D-isomers which are antagonistic to GnRH are being investigated for their potential use as a contraceptive or for regulating conception periods. GnRH antagonists may also be used for the treatment of precocious puberty and endometriosis. Such antagonists have also been found useful to regulate the secretion of gonadotropins in male mammals-and can be employed to arrest spermatogenesis, e.g. as male contraceptives, and for treatment of prostatic hypertrophy. More specifically, GnRH antagonists can be used to treat steroid-dependent tumors, such as prostatic, brain and mammary tumors.

It is desired to provide improved peptides which are strongly antagonistic to endogenous GnRH and which inhibit secretion of LH and the release of steroids by the gonads of mammals. It is also desired to provide compounds which exhibit a longer duration of biological effectiveness in vivo. Further desires are to provide GnRH antagonists which have good solubility in aqueous media, such as saline buffers, and to provide such peptides which exhibit substantial biological potency when administered orally.

SUMMARY OF THE INVENTION

The present invention provides D-isomer-containing peptides which inhibit the release of gonadotropins in mammalians, including humans, and it also provides methods for inhibiting the release of steroids by the gonads of male and female mammalians. These GnRH analogs are referred to as GnRH antagonists because they are strongly antagonistic to GnRH and have an inhibitory effect on the reproduction processes of mammalians. These analogs may be used to inhibit the production and/or secretion of gonadotropins and sex hormones under various circumstances, including precocious puberty, hormone dependent neoplasia, dysmenorrhea, endometriosis and steroid-dependent tumors.

Generally, in accordance with the present invention, peptides have been synthesized which strongly inhibit the secretion of gonadotropins by the pituitary gland of mammalians, including humans, and/or inhibit the release of steroids by the gonads. These peptides are bicyclic analogs of GnRH wherein there are two covalent bonds, i.e., between the 4-position residue and the 10-position residue, and between the 5-position residue and the 8-position residue. Very generally, these GnRH antagonists can be described as peptides having a decapeptide main chain, which peptide is effective to substantially reduce the secretion of LH by the pituitary, said peptide being an analog of mammalian GnRH wherein the N-terminus is preferably acylated, the C-terminus is amidated, a side chain of the residue in the 4-position is connected by a covalent bond to the residue in the 10-position, and the side chain of the residue in the 5-position and the side chain of the residue in the 8-position are connected by amide linkages to the α-carbon of an amino acid residue outside of said main chain.

More specifically, these peptides have β-(2-naphthyl)-D-alanine(hereinafter β-D-2NAL) in the 1-position or an equivalent residue in the 1-position as well known in this art, such as D—Phe, D—Pro, L-Pro, D—Trp or dehydroPro, with dehydroPro being preferred if β-D—NAL is not present. The 1-position residue is preferably modified so that its alpha-amino group contains an acyl group, such as formyl(For), acetyl(Ac), acrylyl(Acr), vinylacetyl(Vac) or benzoyl(Bz); acetyl is preferred; however, an equivalent acyl group can be employed as well known in this art. A modified D—Phe residue is present in the 2-position which has specific modifications as well known in this art, principally substitutions in the benzene ring. Single substitutions for hydrogen in the ring are preferably made in the para or 4-position, but might instead be in either the 2- or 3-position; such substitutions are selected from chloro, fluoro, bromo, methyl, methoxy and nitro, with chloro, fluoro and nitro being preferred. Dichloro substitutions may also be made in the 2,4 or 3,4 positions in the ring. The alpha-carbon atom may also be methylated, e.g. ($C^\alpha Me$/4Cl)Phe.

The residue in the 3-position is a D-isomer such as unsubstituted or substituted D—Trp, D-3PAL, β-D-2NAL or β-D-1NAL. PAL and D—PAL represent the L- and D-isomers of pyridylalanine where the β-carbon of Ala is linked to the 2-, 3- or 4-position, preferably to the 3-position, on the pyridine ring. Although D-3PAL is the preferred residue in the 3-position, a known equivalent can instead be used.

The 4-position residue may be Abu or a dicarboxylic amino acid, preferably Asp, and the residue in the 10-position is, of course, complementary to the 4-position residue. Moreover, a dicarba bond between the residues in the 4- and 10-positions of a length slightly longer or shorter than that provided by a pair of Abu residues may also be employed.

The 5-position is occupied by Glu or Asp or homoglutamic acid (Hgl), preferably Glu, and the 8-position by Dbu or Orn or Dpr, preferably Dbu, with the side chains of these two residues being connected through a peptide linkage, with an additional α-amino acid being included in the linkage between the side chains of these two residues, as explained in detail hereinafter. Generally any α-amino acid may be used; however, those having a basic side chain, such as Arg, Hat, His, 4gua-Phe, gua-4methyl-Phe, 4NH2-Phe(Aph), Lys, Orn and the like, or Phe may be preferred. In addition, there is a class of recently synthesized unnatural α-amino acids which include either a $N^\omega$-cyano-$N^{\omega 1}$-alkyl-(or aryl-) guanidino moiety or an aminotriazole moiety that can also be used, which are referred to as UAA and are described hereinafter in more detail.

The peptide has D—Arg in the 6-position or an equivalent D-isomer chosen from those well known in this art. D-isomers of the aforementioned unnatural α-amino acids (D—UAAs) can also be present in the 6-position. The naturally occurring residue Leu is preferably in the 7-position; however, an equivalent such as Nle, NML, Phe, Nva, Met, Tyr, Trp or PAL can be present.

These GnRH antagonists have good duration of biological activity when tested in vivo. They are considered to have higher potency when administered orally compared to previously available GnRH antagonists. They have good solubility in saline solutions and other aqueous media. The peptides inhibit ovulation of female mammals when administered at low levels at proestrus and are also effective to cause resorption of fertilized eggs if administered shortly after conception. These peptides are also effective for the contraceptive treatment of male mammals and for the treatment of steroid-dependent and other tumors. Thus, they provide for improved methods of pharmaceutical treatment.

DETAILED DESCRIPTION OF THE PREFERRED EMBODIMENTS

More specifically, certain preferred bicyclic peptides of the present invention have the following formula:

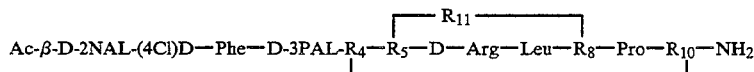

wherein $R_4$ is Asp or Abu; $R_5$ is Glu, Hgl or Asp; $R_8$ is Dbu, Dpr or Orn; $R_{10}$ is Dpr or Abu; and $R_{11}$ is Gly, Ala, Sat, β-Ala, Leu, Hat, Orn, Lys, Dbu, Dpr, Glu, Asp, NAL, (E)Phe, Arg, His, Tyr, Set, Gln, Ash, Val, Nle, Nva, PAL, Ile, Trp, Cys or Cit; with E being defined hereinafter; provided however that when $R_4$ is Abu, $R_{10}$ is Abu; and when $R_4$ is Asp, $R_{10}$ is Dpr. Alternatively $R_{11}$ can be UAA. Preferably when $R_5$ is Glu, $R_8$ is Dbu; when $R_5$ is Asp, $R_8$ is Orn; and when $R_5$ is Hgl, $R_8$ is Dpr.

Taking into account a number of the most common equivalent residues which may alternatively be employed, these GnRH antagonists may have the following general formula:

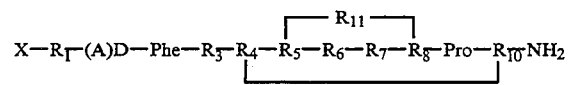

wherein X is hydrogen or an acyl group having 7 or less carbon atoms; $R_1$ is β-D-2NAL or dehydroPro; A is H,Cl, F, NO2, CHhd 3, OCH3, $C^\alpha Me$/4Cl, Cl2 or Br; $R_3$ is β-D-2NAL, D-3PAL or D—Trp; $R_4$ is Asp or Abu; $R_5$ is Glu, Hgl or Asp; $R_6$ is β-D—NAL, (B) D—Trp, (A') D—Phe, (D) D—Hat, D—Tyr, (C) D—His, D—PAL, (D) D—Arg, D—Leu, D—Ile, D—Val, D—Nle, D—Ala, D—Pro, D—Ser(OtBu), D—Nva or D—UAA; A' is A, NH2, NHCH3 or gua; B is H, NO2, NH2, OCH3, F, Cl, Br, CH3, $N^{in}$For or $N^{in}$Ac; C is H, imBzl or dinitrophenyl; D is H or di-lower alkyl; $R_7$ is Nle, Leu, NML, Phe, Met, Nva, Tyr, Trp or PAL; $R_8$ is Dbu, Dpr or Orn; $R_{10}$ is Dpr or Abu; $R_{11}$ is Gly, Ala, Sat, β-Ala, Leu, Mar, Dbu, Dpr, Orn, Lys, Glu, Asp, NAL, (E)Phe, Arg, His, Tyr, Ser, PAL, Gln, Ash, Val, Nle, Nva, Ile, Trp, Cys, Cit or UAA; and E is gua, guaCH2, NH2, H, Cl, F, Br, NO2, CH3, or OCH3; provided however that when $R_4$ is Abu, $R_{10}$ is Abu; and when $R_4$ is Asp, $R_{10}$ is Dpr. Preferably when β-D—NAL is present in the 1-position, D—PAL, D—UAA or a hydrophilic D-amino acid residue, such as 4NH2—D—Phe, 4-guanidino-D-Phe, D—His, D—Arg or D—Hat, is present in the 6-position. When dehydroPro is present in the 1-position, D—PAL, D—UAA, or a D-isomer of a lipophilic amino acid, such as D—Trp, D—Phe, For—D—Trp, NO$_2$—D—Trp, D—Leu, D—Ile, D—Nle, D—Tyr, D—Val, D—Ala, D—Ser(OtBu), β-D—NAL or (imBzl)D—His, is preferably in the 6-position.

By dehydroPro is meant 3,4 dehydroproline, $C_5H_7O_2N$. By β-D—NAL is meant the D-isomer of alanine which is substituted by naphthyl on the β-carbon atom, i.e., also termed 3-D—NAL. Preferably β-D-2NAL is employed wherein the attachment to naphthalene is at the 2-position on the ring structure; however, β-D-1NAL may also be used. PAL represents alanine which is substituted by pyridyl on the β-carbon atom; preferably the linkage is to the 3-position on the pyridine ring. When substituted D—Trp is employed, single substitutions for hydrogen may be made in either the 5- or 6-position, which are selected from chloro, fluoro, bromo, methyl, amino, methoxy and nitro, with chloro, fluoro and nitro being preferred. Alternatively, the indole nitrogen may be acylated, e.g. with formyl (N$^{in}$-For- or 1For-) or with acetyl. N$^{in}$For—D—Trp and 6NO$_2$—D—Trp are the preferred substituted residues. When either D—Arg or D—Har is present in the 6-position, the guanidino side chain can be di-substituted with lower alkyl(C$_1$ to C$_4$), preferably diethyl. By NML is meant N$^\alpha$CH$_3$—L—Leu, and by Cit is meant citrulline, having the formula $CH_2(NHCONH_2)CH_2CH_2CH(NH_2)COOH$. By Abu is meant 2-aminobutyric acid, and by Dbu is meant 2,4-diaminobutyric acid. By Dpr is meant 2,3-diaminopropionic acid. By 4-gua—D-Phe is meant a residue of D—Phe substituted in the para-position by a guanidino group; by (gua-4CH$_2$)D—Phe is meant a residue of D—Phe having a methyl group in the para-position which is itself substituted with a guanidino group.

The unnatural L- or D-isomer α-amino acids (UAAs) have either (a) N$^\omega$-cyano-N$^{\omega 1}$-alkyl-(or aryl-)guanidino moieties formed on p-aminophenylalanine (Aph) or as a part of Hat, Arg or a shortened version of Arg having 1 or 2 fewer CH$_2$-groups, wherein alkyl is preferably lower alkyl (C$_1$ to C$_6$) or cyclohexyl and aryl is preferably benzyl, histaminyl, naphthyl, tryptamino or pyridyl; or (b) an aminotriazole moiety (atz) on the distal amino group of Aph, Lys, Orn, Dbu or Dpr. These UAAs can be synthesized as disclosed in U.S. patent application Ser. No. 545,239, filed June 27, 1990, the disclosure of which is incorporated herein by reference. The biopotency of GnRH antagonists incorporating such UAAs in the main chain was reported in Theobald et al., J. Medical Chemistry, 34, 2395-2402 (1991). Examples of some suitable UAAs which are modified homoarginine molecules include Har(mCN), Har(iCN), Har(bCN), Har(hCN), Har(chCN), Har(2mpCN), Har(eCN) and Har(bzCN) wherein m=methyl, e=ethyl, i=isopropyl, b=butyl, h=hexyl, ch=cyclohexyl, bz=benzyl and 2mp=2-methylpyridyl. Once the UAA is synthesized, the α-amino group of the UAA can be protected with Boc, Fmoc or some other suitable group; the side chain should not normally require protection.

The following general formula defines a preferred subgenus of GnRH antagonists:

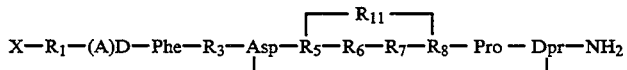

wherein X is hydrogen or an acyl group having 7 or less carbon atoms; R$_1$ is β-D-2NAL or dehydroPro; A is H,Cl, F, NO$_2$, CH$_3$, OCH$_3$, C$^\alpha$Me/4Cl, Cl$_2$ or Br; R$_3$ is β-D-2NAL, D-3PAL or D—Trp; or R$_5$ is Glu, Hgl or Asp; R$_6$ is β-D—NAL, (B) D—Trp, (A')D—Phe, (D)D—Har, D—Tyr, (C) D—His, D—PAL, (D) D—Arg, D—Leu, D—Ile, D—Val, D—Nle, D—Ala, D—Pro, D—Ser(OtBu), D—Nva or D—UAA; A' is A, NH$_2$, NHCH$_3$ or gua; B is H, NO$_2$, NH$_2$, OCH$_3$, F, Cl, Br, CH$_3$, N$^{in}$For or N$^{in}$Ac; C is H, imBzl or dinitrophenyl; D is H or di-lower alkyl; R$_7$ is Nle, Leu, NML, Phe, Met, Nva, Tyr, Trp or PAL; R$_8$ is Dbu, Dpr or Orn; and R$_{11}$ is Gly, Ala, Sar, β-Ala, Leu, Har, NAL, (E) Phe, Arg, His, Tyr, Ser, Gln, Ash, Val, Nle, Nva, Ile, Trp, Cit or UAA; and E is gua, guaCH$_2$, NH$_2$, or H. When R$_1$ is β-D—NAL, then R$_6$ is preferably 4-NH$_2$—D—Phe, D—Har, D—His, 4-gua—D—Phe, D—PAL or D—Arg.

Another preferred group of biologically active bicyclic peptides which have a covalent bond between the residues in the 4- and 10-positions and which have a cyclizing bond containing an α-amino acid residue between the side chains of the residues in the 5- and 8-positions has the following formula:

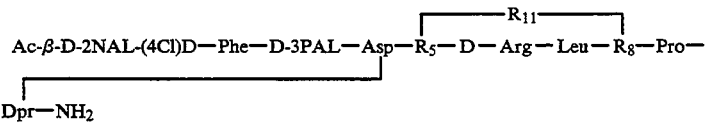

wherein R$_5$ is Glu, Hgl or Asp; R$_8$ is Dbu, Dpr or Orn; and R$_{11}$ is Gly, Ala, Sat, β-Ala, Leu, Hat, NAL, PAL, (E)Phe, Arg, Lys, Orn, Dbu, Dpr, His, Tyr, Set, Gln, Ash, Val, Nle, Nva, Ile, Trp, Cys or Cit. E is as defined hereinbefore, and R$_{11}$ can alternatively be UAA.

Yet another preferred group of biologically active bicyclic peptides has the following formula:

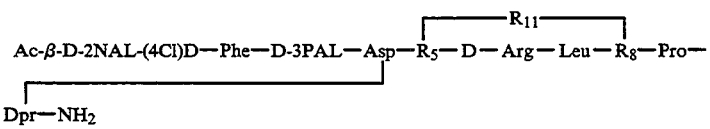

wherein R$_5$ is Asp or Glu; R$_8$ is Dbu or Orn; and R$_{11}$ is Gly, Ala, Lys, Orn, Dbu, Dpr, Sar, β-Ala, Leu, Har, NAL, (E)Phe, Arg, His, Tyr, Ser, PAL, Gln, Asn, Val, Nle, Nva, Ile, Trp, Cys or Cit. E is as defined hereinbefore, and $R_{11}$ can alternatively be UAA.

In a particularly preferred group of bicyclic peptides, the formula is generally as set forth above except that $R_5$ is Asp or Glu and $R_8$ is Dbu or Orn. These bicyclic peptides have the following formula:

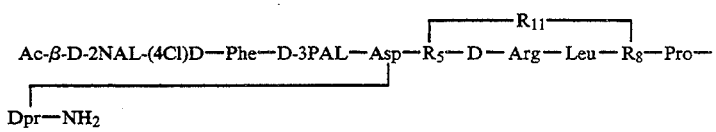

wherein $R_5$ is Asp or Glu; $R_8$ is Dbu or Orn; and $R_{11}$ is a basic α-amino acid.

A presently most preferred group of bicyclic peptides has the following formula:

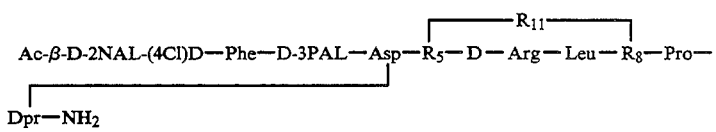

wherein $R_5$ is Asp or Glu; $R_8$ is Dbu or Orn; and $R_{11}$ is (gua)Phe, (guaCH$_2$)Phe, Arg, Har or His, but alternatively $R_{11}$ can be UAA.

It may be desirable to have a slightly shorter or longer cyclizing linkage between the two residues in the 4- and 10-positions than the dicarba linkage between Abu residues, and in such an instance, peptides may be synthesized having the formula:

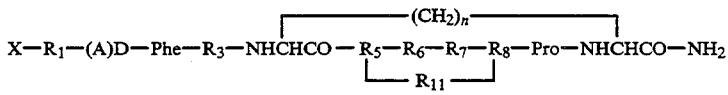

wherein X is hydrogen or an acyl group having 7 or less carbon atoms; $R_1$ is β-D-2NAL or dehydroPro; A is H, Cl, F, NO$_2$, CH$_3$, OCH$_3$, C$^α$Me/4Cl, Cl$_2$ or Br; $R_3$ is β-D-2NAL, D-3PAL or D—Trp; $R_5$ is Glu, Hgl or Asp; $R_6$ is β-D—NAL, (B) D—Trp, (A′)D—Phe, (D)D—Hat, D—Tyr, (C)D—His, D—PAL, (D) D—Arg, D—Leu, D—Ile, D—Val, D—Nle, D—Ala, D—Pro, D—Ser(OtBu), D—Nva or D—UAA; A′ is A, NH$_2$, NHCH$_3$ or gua; B is H, NO$_2$, NH$_2$, OCH$_3$, F, Cl, Br, CH$_3$, N$^{in}$For or N$^{in}$Ac; C is H, imBzl or dinitrophenyl; D is H or di-lower alkyl; $R_7$ is Nle, Leu, NML, Phe, Met, Nva, Tyr, Trp or PAL; $R_8$ is Dbu, Dpr or Orn; $R_{11}$ is Gly, Ala, Sat, β-Ala, Leu, Har, Orn, Lys, Glu, Asp, NAL, (E) Phe, Arg, His, Tyr, Ser, Gln, Ash, PAL, Val, Nle, Nva, Ile, Trp, Cit or UAA; E is gua, guaCH$_2$, NH$_2$, H, Cl, F, Br, NO$_2$, CH$_3$, or OCH$_3$), and n is an integer between 2 and 6 and preferably, n=3 to 5. If the residues in positions 4 and 10 were both Abu, n would equal 4.

The peptides of the present invention can be synthesized by classical solution synthesis or by a solid phase technique using a chloromethylated resin, a hydroxymethylated resin, a methylbenzhydrylamine resin (MBHA), a benzhydrylamine (BHA) resin or any other suitable resin known in the art. The solid phase synthesis is conducted in a manner to stepwise add the amino acids in the chain in the manner set forth in detail in U.S. Pat. No. 4,211,693. Side-chain protecting groups, as are well known in the art, are preferably added to the residues to be employed in the synthesis having particularly labile side chains and may optionally be added to others, such as Trp, before these amino acids are coupled to the chain being built upon the resin. Such synthesis provides the fully protected intermediate peptidoresin.

The "final" chemical intermediates made generally in accordance with the preferred procedure for producing bicyclic peptides having certain features of the invention are represented by Formula II:

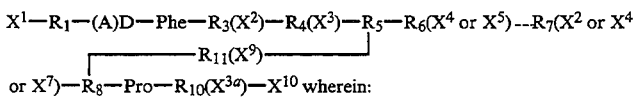

$X^1$ is an alpha-amino protecting group of the type known to be useful in the art in the stepwise synthesis of polypeptides. Among the classes of alpha-amino protecting groups covered by $X^1$ are (1) acyl-type protecting groups, such as formyl(For), trifluoroacetyl, phthalyl, p-toluenesulfonyl(Tos), benzoyl(Bz), benzenesulfonyl, o-nitrophenylsulfenyl(Nps), tritylsulfenyl, o-nitrophenoxyacetyl, acrylyl(Acr), chloroacetyl, acetyl(Ac) and γ-chlorobutyryl; (2) aromatic urethan-type protecting groups, e.g., benzyloxycarbonyl(Z), fluorenylmethyloxycarbonyl(Fmoc) and substituted benzyloxycarbonyl, such as p-chlorobenzyloxy-carbonyl(ClZ), p-nitrobenzyloxycarbonyl, p-bromobenzyloxycarbonyl and p-methoxybenzyloxycarbonyl; (3) aliphatic urethan protecting groups, such as tertbutyloxycarbonyl(Boc), diisopropylmethoxycarbonyl, isopropyloxycarbonyl, ethoxycarbonyl and allyloxycarbonyl; (4) cycloalkyl urethan-type protecting groups, such as cyclopentyloxycarbonyl, adamantyloxycarbonyl and cyclohexyloxycarbonyl; (5) thiourethan-type protecting groups, such as phenylthiocarbonyl; (6) alkyl-type protecting groups, such as allyl(Aly), triphenylmethyl(trityl) and benzyl(Bzl); (7) trialkylsilane groups, such as trimethylsilane. The preferred alpha-amino protecting group is Boc, except for the protection of the α-amino group of $R_{11}$.

$X^2$ is hydrogen or a suitable protecting group for the indole nitrogen of Trp, such as Bz.

$X^3$ is a suitable, preferably hydrazine-labile, direct bond between the residues $R_4$ and $R_{10}$. $X^{3a}$ is an protecting group for a carboxyl side chain, such as OChx(cyclohexyl ester) or OBzl(benzyl ester); or is a acid-labile protecting group for an amino group, e.g. 2Cl—Z or t-amyloxycarbonyl, or is a direct bond between residues $R_4$ and $R_{10}$.

$X^4$ is hydrogen or a protecting group for the phenolic hydroxyl group of Tyr selected from the group consisting of tetrahydropyranyl, tert-butyl, trityl, benzyl, Z, 2-bromobenzyloxycarbonyl (2BrZ) and 2,6-dichlorobenzyl(DCB). 2BrZ is preferred.

$X^5$ is a protecting group for a side chain guanidino group in Arg or the like, or for the imidazole group of His, such as nitro, Tos, trityl, adamantyloxycarbonyl, Z and 2,4-dinitrophenyl(DNP), or $X^5$ may be hydrogen, which means there is no protection on the labile side chain group. Tos is generally preferred.

$X^6$ is a base-labile protecting group for a carboxyl group, preferably fluorenylmethyl ester (OFm).

$X^7$ is hydrogen or a protecting group for Met, such as oxygen.

$X^8$ is a base-labile protecting group for an amino group, preferably Fmoc. Neither $X^6$ nor $X^8$ appears in the "final" intermediate.

$X^9$ is hydrogen or a suitable side chain-protecting group as described above or as generally known in this art.

$X^{10}$ may be O—$CH_2$—[resin support], —NH—[resin support], OH, ester or $NH_2$.

The criterion for selecting side-chain protecting groups for $X^2$-$X^9$ is that the protecting group should be stable to the reagent under the reaction conditions selected for removing the alpha-amino protecting group (e.g. Boc) at each step of the synthesis. Generally, the protecting group should not be split off under coupling conditions but will be removed upon completion of the synthesis of the desired amino acid sequence under reaction conditions that will not alter the peptide chain; however, certain of the protecting groups, e.g. $X^6$ and $X^8$, are chosen to be removable without the removal of other of the protecting groups in some syntheses.

When the $X^{10}$ group is —O—$CH_2$—[resin support], the ester moiety of one of the many functional groups of a polystyrene resin support is being represented. When the $X^{10}$ group is —NH—[resin support], an amide bond connects $R_{10}$ to a BHA resin or to a MBHA resin.

When the N-terminus is acylated, as is preferably the case, a reaction is preferably carried out with the intermediate peptide on the resin (after removing the Boc-protection from the N-terminal alpha-amino group while the labile side chains remain protected), e.g. by reacting with acetic acid in the presence of dicyclohexyl carbodiimide (DCC) or preferably with acetic anhydride, or by another suitable reaction as known in the art, to attach an acetyl group.

The bicyclic peptides can be made using various protocols as generally known in this art. For example, U.S. Pat. No. 5,064,939, issued Nov. 12, 1991, the disclosure of which is incorporated herein by reference, discloses a variety of suitable protocols depending upon the character of the bond between the residues in the 4- and 10-positions. Likewise, the incorporation of the alpha-amino acid in the linkage between the residues in the 5- and 8-positions can be accomplished in several different ways, for example, by using an appropriately blocked dipeptide when adding the residue that will occupy either the 8- or the 5-position in the step-by-step peptide building sequence; however, to avail oneself of commercially available starting materials, it may be advantageous to add this "nonbackbone" alpha-amino acid to either the residue in the 8-position or the residue in the 5-position after it has been incorporated into the main chain of the peptide being synthesized.

Very generally, the preferred bicyclic peptides are made by carrying out solid-phase synthesis on a suitable resin and performing at least one cyclizing step while the peptide intermediate is a part of the peptidoresin, and preferably before the entire peptide has been synthesized. After this first cyclization is effected, the synthesis of the decapeptide main chain is completed. At such time, if the bond between the 4- and 10-position residues is of the dicarba type (as discussed hereinafter), the second cyclization will have been completed. If the bond being established between the 4- and 10-position residues is an amido bond, cyclization may be carried out on the resin, but it is preferably effected following cleavage. Accordingly, the protected peptide would then be suitably cleaved from the resin. For example, if a hydroxymethylated resin or a chloromethylated resin support is used, cleavage by ammonolysis is used, as is well known in the art, to yield the fully protected, C-terminally amidated intermediate; alternatively, if a benzhydrylamine resin is used, treatment with hydrofluoric acid (HF) causes deprotection of side chains as well as cleavage of the peptide from the resin as a C-terminal amide.

As indicated above, it is generally preferred to carry out the final cyclizing step to form the bond between the position 4- and 10-residues following the cleavage from the resin. When the cyclization is via creating an amide bond between a side-chain carboxyl group of the 4-position residue and a side-chain amino group of the 10-position residue (which is the presently preferred bond), it is preferable to synthesize the protected peptide on an MBHA or BHA resin and to derivatize a cyclohexyl or benzyl ester protecting group of the carboxyl acid side chain to form a hydrazide while the peptide is still attached to the resin. This can be accomplished by using OChx or OBzl as a protecting group for the carboxyl side-chain of the residue to be involved in the amide-bond bridge. Following this selective hydrazide activation, deprotection of the remainder of the side-chain protecting groups and cleavage from the resin are effected. Then reaction to accomplish cyclization is carried out by treating with isoamylnitrite and a strong acid, such as HCl, to generate the azide which in turn reacts with the free amino group on the side chain of the 4-position residue to ultimately generate the amide bond.

Analogs of GnRH which include the equivalent of modified cystsine residues in the 4- and 10-positions wherein the disulfide linkage has been replaced by —$CH_2$—linkage are referred to as dicarba. In general, syntheses of cyclic peptides of this particular type are exemplified by the teachings of the following U.S. Pat. Nos. 4,115,554 (Sep. 19, 1978); 4,133,805 (Jan. 9, 1979); 4,140,767 (Feb. 20, 1979); 4,161,521 (Jul. 17, 1979); 4,191,754 (Mar. 4, 1980); 4,238,481 (Dec. 9, 1980); 4,244,947 (Jan. 13, 1981); and 4,261,885 (Apr. 14, 1981).

As a comparison of the ultimate peptide to one having a Cys—Cys disulfide bond, the location which would be occupied by a Cys residue instead contains a residue of alpha-amino butyric acid(Abu). When preparing peptides having such a dicarba linkage or a longer or shorter chain dicarba-type linkage, the procedure set forth in either U.S. Pat. No. 4,161,521 or U.S. Pat. No. 4,703,106 is preferably employed (the disclosures of which patents are incorporated herein by reference). In the peptide intermediate so synthesized, $X^3$ and $X^{3a}$ represent a direct bond via one side chain to the other residue.

It has been found to be particularly advantageous to carry out the solid-phase synthesis of certain of these preferred bicyclic GnRH antagonist peptides having an amide linkage between the 4- and 10-position residues using an MBHA resin or the equivalent. After attaching the first 5 residues of the main chain, i.e. the residues which will occupy positions 6-10 of the GnRH antagonists, the "nonbackbone" residue is added. The side chain amino group of the 10-position residue is appropriately blocked with benzyloxycarbonyl (Z) or an equivalent protecting group that will not be removed under basic conditions. Boc or an equivalent is used as the alpha-amino protecting group for all of the amino acids in the main chain, and the side chain amino group of the 8-position residue is protected with Fmoc. Following the creation of the pentapeptide, the Fmoc protection on the side chain amino group of this residue in the main chain of the pentapeptide is removed using piperidine, and the nonbackbone residue (which has its alpha-amino group protected by Fmoc and has any labile side chain appropriately protected) is coupled to the side chain of the 8-position residue using standard coupling conditions.

Following this coupling, the Boc-protecting group is removed from the 6-position residue, and the 5-position residue is added, having its carboxyl side chain protected with OFm. Following this coupling step, the Fmoc and OFm side chain protecting groups are removed by treatment with piperidine, and then cyclicization is effected by treatment with BOP [Benzotriazolyl-N-oxytris(dimethylamino)-phosphoniu, hexafluorophosphate] and diisopropylethylamine. Following cyclicization, the BOC-protecting group is removed from the N-terminus of the hexapeptide main chain, and the synthesis of the decapeptide main chain is completed using OBzl or OChx as the side chain carboxyl protecting group for the 4-position residue. Thereafter, following completion of the decapeptide main chain, and then removal of the Boc protecting group at the N-terminus and acylation thereof, the peptidoresin is treated for about 60 hours at room temperature with hydrazine in order to form the hydrazide on the side chain of the 4-position residue. Thereafter, the peptidoresin is treated with HF to remove the remaining protecting groups and cleave the peptide from the resin. Finally, treatment with HCl and isoamylnitrate at a temperature below 0° C., followed by the addition of N,N-diisopropylethylamine is used to effect an azide coupling reaction, which results in creation of an amide bond between the side chains of the residues in the 4- and 10-positions.

Thus, for example, the invention also provides a method for making certain preferred bicyclic peptides or nontoxic salts thereof, which peptides have the Formula I:

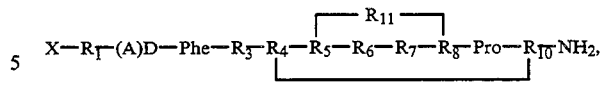

wherein X is hydrogen or an acyl group having 7 or less carbon atoms; $R_1$ is β-D-2NAL or dehydroPro; A is H,Cl, F, $NO_2$, $CH_3$, $OCH_3$, $C^\alpha Me/4Cl$, $Cl_2$ or Br; $R_3$ is β-D-2NAL, D-3PAL or D—Trp; $R_4$ is Asp or Abu; $R_5$ is Glu, Hgl or Asp; $R_6$ is β-D—NAL, (B) D—Trp, (A')D—Phe, (D) D—Har, D—Tyr, (C)D—His, D—PAL, (D) D—Arg, D—Leu, D—Ile, D—Val, D—Nle, D—Ala, D—Pro, D—Ser(OtBu), D—Nva or D—UAA; A' is A, $NH_2$, $NHCH_3$ or gua; B is H, $NO_2$, $NH_2$, $OCH_3$, F, Cl, Br, $CH_3$, $N^{in}For$ or $N^{in}Ac$; C is H, imBzl or dinitrophenyl; D is H or all-lower alkyl; $R_7$ is Nle, Leu, NML, Phe, Met, Nva, Tyr, Trp or PAL; $R_8$ is Dbu, Dpr or Orn; $R_{10}$ is Dpr or Abu; $R_{11}$ is Gly, Ala, Sat, β-Ala, Leu, Hat, Orn, Lye, Dbu, Dpr, PAL, Glu, Asp, NAL, (E) Phe, Arg, His, Tyr, Ser, Gln, Asn, Val, Nle, Nva, Ile, Trp, Cys, Cit or UAA; and E is gua, $guaCH_2$, $NH_2$, H, Cl, F, Br, $NO_2$, $CH_3$, or $OCH_3$; provided however that when $R_4$ is Abu, $R_{10}$ is Abu; and when $R_4$ is Asp, $R_{10}$ is Dpr; which method comprises (a) forming a first intermediate compound having the formula:

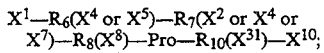

(b) removing ($X^8$) and coupling ($X^8$)$R_{11}$($X^9$) to the side chain of $R_8$; (c) coupling $R_5$ to $R_6$ to create a second intermediate having the formula:

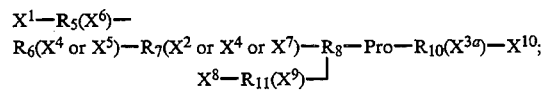

(d) removing ($X^6$) from $R_5$ and $X^8$ from $R_{11}$ and creating a cyclizing amide bond; (e) then forming a third intermediate compound having the Formula II:

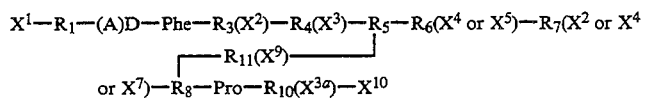

wherein $X^1$ is hydrogen or an alpha-amino protecting group; $X^2$ is hydrogen or a protecting group for an indole nitrogen; $X^3$ and $X^{3a}$ are a direct bond between $R_4$ and $R_{10}$ or acid-labile protecting groups for carboxyl or amino side chains; $X^4$ is hydrogen or a protecting group for a phenolic hydroxyl group of Tyr; $X^5$ is hydrogen or a protecting group for a guanidino or imidazole side chain; $X^6$ is a base-labile protecting group for a carboxyl group; $X^7$ is a protecting group for Met; $X^8$ is a base-labile protecting group for an amino moiety; $X^9$ is hydrogen or an appropriate side chain protecting group; and $X^{10}$ is selected from the group consisting of $O—CH_2$—(resin support), —NH—(resin support), esters, and amides; (f) converting $X^3$ to a hydrazide; (g) splitting off any remaining protecting groups and cleaving from said resin support; (h) creating a cyclizing bond between $R_4$ and $R_{10}$ and, if desired, (i) converting a resulting peptide into a nontoxic salt thereof. The so-called "final" intermediate for certain preferred bicyclic peptides is that having the formula:

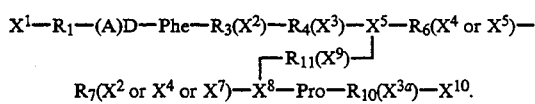

$R_7(X^2$ or $X^4$ or $X^7)$—$X^8$—Pro—$R_{10}(X^{3a})$—$X^{10}$.

Purification of the peptide may be effected by ion exchange chromatography on a CMC column, followed by partition chromatography using the elution system: n-butanol; 0.1N acetic acid (1:1 volume ratio) on a column packed with Sephadex G-25. Purification is preferably carried out by using RP—HPLC as known in this art, and as set forth specifically in J. Rivier, et al. *J. Chromatography*, 288 (1984) 303-328.

The peptides of the invention are considered to be effective to prevent ovulation in female rats when administered at about noon on the day of proestrus, at levels of less than 100 micrograms per kilogram of body weight. For prolonged suppression of ovulation, it may be desirable to use dosage levels in the range of from about 0.1 to about 2.5 milligrams per kilogram of body weight per day. These antagonists are also effective to arrest spermatogenesis when administered to male mammals on a regular basis and can thus be used as contraceptives. Since these compounds will reduce testosterone levels (an undesired consequence in the normal, sexually active male), it may be reasonable to administer replacement dosages of testosterone along with the GnRH antagonist. These antagonists can also be used to regulate the production of gonadotropins and sex steroids for other purposes as indicated hereinbefore.

These improved bicyclic GnRH antagonists are generally characterized by a substantial ability to suppress the secretion of LH in a standard rat pituitary cell assay when administered together with a concentration of 3 nanomolar GnRH, the details of which assay are set forth in Rivier and Vale, *Life Sciences*, 23, 869-876 (1978). By substantial ability is meant that, at a concentration of GnRH antagonist to GnRH of about 2/1 or less, the amount of LH secreted is reduced by 50% ($IDR_{50}$). Moreover, when tested in vivo in the standard rat anti-ovulation assay (Corbin et al. *Endocrine Res. Commun.*, 2, 1 (1975)), these GnRH antagonists show complete blockage of ovulation when administered at about 200 μg or less per kilogram of body weight.

The following examples set forth preferred methods for synthesizing GnPH antagonists using the solid-phase technique. These examples illustrate the best mode presently known to the inventors for making these peptides; however, as indicated hereinbefore, alternative methods of syntheses are available and can be employed, including classical solution-phase synthesis. Accordingly, these examples should be considered as illustrative to be taken into consideration in conjunction with the remainder of this specification and not as limiting.

EXAMPLE I

Bicyclic peptides as set forth in TABLE I having the formula:

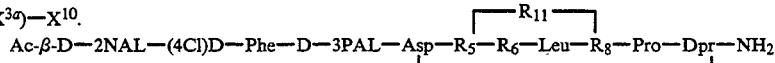

are prepared by the solid-phase procedure referred to above.

TABLE I

| No. | $R_5$ | $R_6$ | $R_8$ | $R_{11}$ |
|---|---|---|---|---|
| 1 | Glu | D-Arg | Dbu | Arg |
| 2 | " | " | " | Gly |
| 3 | Asp | " | " | " |
| 4 | " | " | " | β-Ala |
| 5 | Glu | " | " | Sar |
| 6 | " | " | Dpr | Phe |
| 7 | " | " | Dbu | " |
| 8 | " | " | Orn | " |
| 9 | Asp | " | Dbu | " |
| 10 | " | " | Orn | " |
| 11 | Glu | " | Dbu | β-2NAL |
| 12 | " | " | " | His |
| 13 | " | β-D-2NAL | " | Arg |
| 14 | " | D-Arg | " | (4Cl)Phe |
| 15 | Asp | D-Trp | Dpr | Har |
| 16 | Glu | D-3PAL | Dbu | (gua)Phe |
| 17 | " | D-Ar | " | Aph(atz) |

For purposes of an example, a representative solid phase synthesis of Peptide No. 1 above, which is referred to as (Cyclo 4-10,5,5'-8)[Ac-β-D-2NAL$^1$, (4Cl)D—Phe$^2$, D-3PAL$^3$, Asp$^4$, Glu$^5$(Arg), D—Arg$^6$, Dbu$^8$, Dpr$^{10}$]-GnRH is set forth hereinafter. This peptide has the following formula:

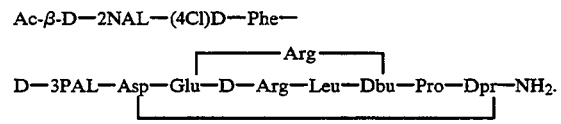

The other peptides in the table are similarly synthesized and purified.

Four grams of MBHA resin are used, and Boc-protected Dpr is coupled to the resin over about a 3-hour period in mixture of dimethylformamide (DMF) and dichloromethane (DCM) in about equal parts using a 3-fold excess of Boc derivative and DCC as an activating reagent. The Dpr residue attaches to the MBHA resin by an amide bond.

Following the coupling of each amino acid residue, washing, deblocking and coupling of the next amino acid residue is carried out in accordance with the following schedule, using an automated machine and the amounts stated, when beginning with about 4-5 grams of resin:

| STEP | REAGENTS AND OPERATIONS | MIX TIMES MIN. |
|---|---|---|
| 1 | DCM wash-80 ml. (2 times) | 3 |
| 2 | Methanol(MeOH) wash-30 ml. (2 times) | 3 |
| 3 | DCM wash-80 ml. (3 times) | 3 |
| 4 | 50 percent TFA plus 5 percent 1,2-ethanedithiol in DCM-70 ml. (2 times) | 10 |
| 5 | Isopropyl alcohol + 1% ethanedithiol wash-80 ml. (2 times) | 3 | the N-terminus of cyclic peptide, and the synthesis of the remainder of the decapeptide main chain is completed to produce the further intermediate:

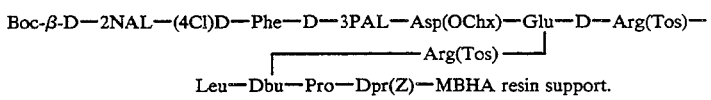

| STEP | REAGENTS AND OPERATIONS | MIN. MIX TIMES |
|------|-------------------------|----------------|
| 6 | TEA 12.5 percent in DCM-70 ml. | 5 |
| 7 | MeOH wash-40 ml. | 2 |
| 8 | TEA 12.5 percent in DCM-70 ml. | 5 |
| 9 | DCM wash-80 ml. (3 times) | 3 |
| 10 | Boc-amino acid (10 mmoles) in 30 ml. of either DMF:DCM or DMF alone, depending upon the solubility of the particular protected amino acid, plus DCC (10 mmoles) in DCM | 30–300 |
| 11 | MeOH wash-40 ml. (2 times) | 3 |
| 12 | TEA 12.5 percent in DCM-70 ml. | 3 |
| 13 | MeOH wash-30 ml. (2 times) | 3 |
| 14 | DCM wash-80 ml. (2 times) | 3 |

The above schedule is used for coupling each of the amino acids of the peptide after the first amino acid has been attached. $N^\alpha$Boc protection is used for each of the remaining amino acids throughout the synthesis, except for Arg which is protected with Fmoc. The side chain of Arg or D—Arg is protected with Tos. Fmoc is used as a side-chain protecting group for the amino group of Dbu; whereas Z is used to protect the side-chain amino group of Dpr. The carboxyl group of the side chain of Glu is protected with OFm, whereas the carboxyl group of the side chain of Asp is protected with OChx. $N^\alpha$Boc-β-D-2NAL is introduced as the final amino acid and is prepared by a method known in the art, e.g. as described in detail in U.S. Pat. No. 4,234,571, issued Nov. 18, 1980. All the amino acids are coupled using a DMF:DCM mixture, except for Boc—D—Arg(Tos), which is coupled in DMF.

Following the assembly of a pentapeptide main chain intermediate on the MBHA resin, having the formula: Boc—D—Arg(Tos)—Leu—Dbu(Fmoc)—Pro—Dpr(-Z)—MBHA resin support, the deprotection of the Dbu side chain is carried out by treatment with about 50 ml of 20 volume % piperidine in DMF for 15 minutes at about 22° C., followed by washing. Following the removal of the side-chain protecting group on Dbu, $N^\alpha$Fmoc-Arg(Tos) is added under standard coupling conditions so that the alpha-carboxyl group forms an amide bond to the side chain amino group on the Dbu residue.

Following washing in the usual manner, the synthesis of the main chain of the peptide is continued by the addition of $N^\alpha$Boc—Glu(OFm) under standard coupling conditions. Following washing, the peptidoresin is treated with about 50 milliliters of 20 volume percent piperidine in DMF for about 15 minutes at room temperature, followed by washing, to remove the Fmoc protecting group on the alpha-amino group of Arg and the OFm protecting group on the side chain of Glu. Then the peptidoresin is suspended with about 5 meq. (2.2 gm) of BOP [Benzotriazolyl-N-oxytris(dimethylamino)-phosphonium hexafluorophosphate] and 15 meq. of diisopropylethylamine and stirred for about 4 hours at 65° C. and then overnight at room temperature to effect cyclization between the side chain of Glu and the α-amino group of Arg. The peptidoresin is filtered and then washed with DMF, MeOH, DCM and MeOH. Thereafter, the Boc-protecting group is removed from the N-terminus of cyclic peptide, and the synthesis of the remainder of the decapeptide main chain is completed to produce the further intermediate:

After deblocking the alpha-amino group at the N-terminus using trifluoroacetic acid(TFA), acetylation is achieved using a large excess of acetic anhydride in dichloromethane. This resultant product is sometimes referred to as the "final" intermediate. Thereafter, about 4 g. of protected-peptidyl resin is suspended at room temperature in 40 ml of DMF, and 1 ml. of anhydrous hydrazine (30–40x excess) is added to it under continuous stirring. Nitrogen is bubbled through the reaction mixture, and continuous stirring is effected in a closed vial for about 3 days. The resin is filtered, washed 3 times with DMF, twice with MeOH, and 3 times with DCM, and then finally dried.

About 4 g. of the protected peptide-hydrazide-resin is treated with 100–150 ml of distilled HF, in the presence of 10 ml of anisole as a scavenger, at 0° C. for about 40 minutes to remove the remaining protecting groups and cleave the peptide from the resin. HF is removed under high vacuum, and the peptide is precipitated with anhydrous ethyl ether. The solid material is collected, dissolved in 50 ml $CH_3CN:H_2O$ (1:1) and lyophilized. It is then purified using RP—HPLC prior to final cyclizing.

1000 mg of the peptide-hydrazide is dissolved in 15 ml of DMF and cooled to about −25° C., and $N_2$ gas is bubbled therethrough. 0.56 ml (about 2.25 mmol) of 4N HCl in dioxane is added, and finally 105 μl (about 0.78 mmol) of isoamylnitrite is added over ten minutes. Stirring at −25° C. is continued for 3 hours. The azide-solution is diluted with 1000 ml of precooled DMF (−25° C.); N,N-diisopropylethylamine is added in suitable portions to give a final pH of 7.8. The pH is checked and readjusted several times.

The solution is stored at 4° C. for 3 days, then evaporated to dryness in high vacuum. The residue is triturated in the presence of ethyl ether, and the solid is collected and dried in vacuum.

Final purification of the peptide is then effected by analytical and preparative RP—HPLC separations. The analytical HPLC preferably uses a TEAP (triethylammonium phosphate) buffer system, and the preparative HPLC uses a TEAP buffer system followed by a TFA buffer system, as described in detail in the *J. Chromatography* article.

The peptide is Judged to be homogeneous using thin layer chromatography and several different solvent systems, as well as by reversed-phase high performance liquid chromatography using an aqueous triethylammonium phosphate solution plus acetonitrile. Amino acid analysis of the resultant, purified peptide is consistent with the formula for the prepared structure, showing substantially integer-values as expected for each amino acid. The optical rotation of Peptide No. 1 is measured on a photoelectric polarimeter as $[\alpha]_D^{22} = -42° \pm 1 (c=0.72, 50\%$ acetic acid).

The peptides from Table I are assayed in vivo and are also tested in vitro using dissociated rat pituitary cells maintained in culture for 4 days prior to the assay. The levels of LH mediated in response to the application of peptides is assayed by specific radioimmunoassay for rat LH, as set forth in detail in *Life Sciences,* supra. Control dishes of cells only receive a measure which is 3 nanomolar in GnRH; experimental dishes receive a measure 3 nanomolar in GnRH plus a measure having either the present standard antagonist for comparison purposes, i.e. [Ac-dehydroPro$^1$, (4F) D—Phe$^2$, D—Trp$^{3,6}$]—GnRH, or the test peptide, in concentrations ranging from 0.01 to 10 nanomolar. The amount of LH secreted in the samples treated only with GnRH is compared with that secreted by the samples treated with the antagonist peptide plus GnRH. The ability of the test peptide to reduce the amount of LH released by 3 nanomolar GnRH is compared to that of the present standard peptide. All of the peptides exhibit substantial biological potency for inhibiting the release of LH in such in vitro assays.

In vivo testing determines effectiveness to prevent ovulation in female rats. In this test, a specified number of mature female Sprague-Dawley rats, e.g. usually five to ten, each having a body weight from about 225 to 250 grams, is injected with a specified microgram dosage of peptide in either saline or bacteriostatic water at about noon on the day of proestrus. Proestrus is the afternoon of ovulation. A separate female rat group is used as a control to which the peptide is not administered. Each of the control female rats ovulates on the evening of proestrus, and the number of the treated rats which ovulate is recorded. The results are set forth in the following Table A, wherein the dosages stated are in micrograms per rat.

TABLE A

| Peptide No. | Dosage | Rats Ovulating | Dosage | Rats Ovulating |
|---|---|---|---|---|
| 1. | 2.5 | 0/4 | 1.0 | 2/11 |
| 2. | 25 | 0/3 | 10 | 1/6 |
|  | 5 | 2/8 | 2.5 | 6/8 |
| 3. | 25 | 0/5 | 10 | 4/6 |
| 4. | 10 | 4/5 | 5 | 7/10 |
|  |  |  | 2.5 | 9/14 |
| 5. | 10 | 4/9 |  |  |
| 6. | 10 | 6/8 |  |  |
| 7. | 10 | 0/9 | 5 | 1/8 |
|  | 2.5 | 3/10 | 1.0 | 4/7 |
| 8. | 25 | 0/8 | 10 | 5/5 |
| 9. | 10 | 0/4 |  |  |
| 10. | 5 | 0/4 | 2.5 | 6/6 |
| 11. | 10 | 0/4 | 5 | 1/7 |
| 12. | 2.5 | 3/8 | 1.0 | 4/4 |
| 13. | 10 | 5/6 | 2.5 | 7/7 |
| 14. | 5 | 0/6 | 2.5 | 3/4 |

Peptide No. 1 is considered to be significantly effective to prevent ovulation of female rats at a very low dosage. It is considered to be totally effective at a dose of about 50 micrograms per Kg of body weight, and it should likely be effective at about 5 μg/Kg. All of the peptides listed in Table I are considered effective to block GnRH-induced LH secretion and to prevent the ovulation of female mammals at dosages of about 200 μg/Kg of body weight or less.

EXAMPLE II

Peptides as indicated in TABLE II having the formula:

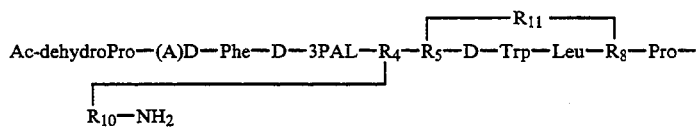

are prepared by the solid-phase procedure referred to above.

TABLE II

|  | A | $R_4$ | $R_5$ | $R_8$ | $R_{10}$ | $R_{11}$ |
|---|---|---|---|---|---|---|
| 18 | 4F | Asp | Asp | Orn | Dpr | Gly |
| 19 | " | " | " | " | " | Phe |
| 20 | " | Abu | Hgl | Dpr | Abu | His |
| 21 | " | " | " | " | " | Arg |
| 22 | " | Asp | " | " | Dpr | Asn |
| 23 | 4Br | " | Asp | Orn | " | Met |
| 24 | " | Abu | " | " | Abu | Nle |
| 25 | H | " | " | " | " | Leu |
| 26 | 4NO$_2$ | " | Glu | Dbu | " | Nva |
| 27 | " | Asp | " | " | Dpr | Tyr |
| 28 | 2,4Cl$_2$ | " | " | " | " | Trp |
| 29 | " | " | Hgl | Dpr | " | 3PAL |
| 30 | C$^\alpha$Me/4Cl | Abu | " | " | Abu | 2NAL |
| 31 | 3,4Cl$_2$ | " | " | " | Abu | Val |

The peptides listed in Table II are considered effective to block GnRH-induced LH secretion in vitro at reasonable concentrations. All of the peptides are considered to be effective to prevent ovulation of female mammals at low dosages.

EXAMPLE III

Peptides as indicated in TABLE III having the formula:

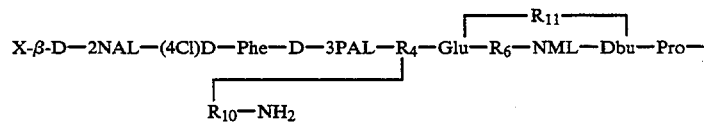

are prepared by the solid-phase procedure referred to above.

TABLE III

|  | X | $R_4$ | $R_6$ | $R_{10}$ | $R_{11}$ |
|---|---|---|---|---|---|
| 32 | Ac | Abu | D-Arg(bCN) | Abu | Lys |
| 33 | Acr | Abu | D-Aph(iCN) | Abu | Orn |
| 34 | For | Asp | D-Aph(atz) | Dpr | Phe |
| 35 | Bz | " | D-Arg(iCN) | " | Sar |
| 36 | Ac | " | D-His | " | Ser |
| 37 | Vac | " | (Et$_2$)D-Har | " | Gln |
| 38 | Acr | " | D-Lys(atz) | " | Ile |
| 39 | Ac | Abu | D-Aph(bzCN) | Abu | Val |
| 40 | Acr | " | D-Dbu(atz) | " | Glu |
| 41 | Ac | " | D-Arg(bzCN) | " | Gly |
| 42 | " | " | D-2PAL | " | Nle |
| 43 | Vac | " | D-Aph(bCN) | " | Cit |
| 44 | Bz | Asp | D-Har | Dpr | Leu |

Peptides such as Nos. 32 and 33 are synthesized by employing the general teaching of U.S. Pat. No. 4,161,521.

Each of the peptides listed in Table III is considered effective to block GnRH-induced LH secretion in vitro at a reasonable concentration. All of the peptides are considered to be effective to prevent ovulation of female mammals at low dosages.

EXAMPLE IV

Peptides as indicated in TABLE IV having the formula:

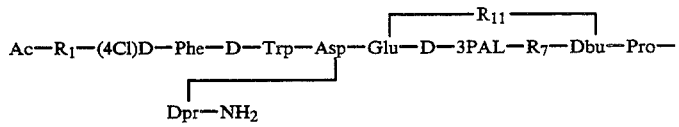

are prepared by the solid-phase procedure referred to above.

TABLE IV

|    | $R_1$ | $R_7$ | $R_{11}$ |
|----|-------|-------|----------|
| 45 | β-D-2NAL | Nle | Arg(bCN) |
| 46 | (1Ac)D-Trp | Met | Har(iCN) |
| 47 | (6Br)D-Trp | Tyr | Har(mCN) |
| 48 | (5F)D-Trp | Nle | (4F)Phe |
| 49 | (6NO$_2$)D-Trp | Met | Aph(iCN) |
| 50 | (5Cl)D-Trp | Tyr | (gua4CH$_2$)phe |
| 51 | (4Cl)D-Phe | Phe | Aph(atz) |
| 52 | (4F)D-Phe | 4F-D-Phe | Lys(atz) |
| 53 | (2,4Cl$_2$)D-Phe | NML | His |
| 54 | dehydroPro | Nle | Dpr(atz) |
| 55 | β-D-1NAL | Trp | Har |
| 56 | (6OCH$_3$)D-Trp | Leu | Dbu(atz) |
| 57 | (5NH$_2$)D-Trp | Nva | Arg(eCN) |
| 58 | (4NO$_2$)D-Phe | NML | Lys |
| 59 | Pro | Tyr | Har(bzCN) |

When peptides such as Nos. 58 and 59 are synthesized, the amino side chain of the $R_{11}$ residue, e.g., Lys, is blocked with a protecting group, such as alloc, which is not removed during HF cleavage from the resin, but which is instead removed later following completion of the second cyclizing bond.

All peptides listed in Table IV are considered effective to block GnRH-induced LH secretion in vitro at a reasonable concentration. All of the peptides are considered to be effective to prevent ovulation of female mammals at low dosages.

EXAMPLE V

Peptides as indicated in TABLE V having the formula:

Ac-β-D—2NAL—(4F)D—Phe—R$_3$—Asp—Glu—R$_6$—Tyr—Dbu—Pro—Dpr—NH$_2$ with R$_{11}$ bridging are prepared by the solid-phase procedure referred to above.

TABLE V

|    | $R_3$ | $R_6$ | $R_{11}$ |
|----|-------|-------|----------|
| 60 | (6NO$_2$)D-Trp | D-Arg(mCN) | (gua4CH$_2$)Phe |
| 61 | (5CH$_3$)D-Trp | (DNP)D-His | Lys(atz) |
| 62 | (5OCH$_3$)D-Trp | (4gua)D-Phe | (4gua)Phe |
| 63 | β-D-2NAL | (6NO$_2$)D-Trp | Arg(bzCN) |
| 64 | β-D-1NAL | D-Aph(atz) | Arg(iCN) |
| 65 | (1For)D-Trp | (Et$_2$)D-Arg | Har(chCN) |
| 66 | (5F)D-Trp | (5NH$_2$)D-Trp | Cit |
| 67 | (5Cl)D-Trp | D-Aph(atz) | Aph(bCN) |
| 68 | D-2PAL | D-Nle | (4NH$_2$)Phe |
| 69 | (1Ac)D-Trp | (4F)D-Phe | Aph(bzCN) |
| 70 | D-3PAL | D-Aph(eCN) | (4CH$_3$)Phe |
| 71 | " | (4NHCH$_3$)D-Phe | Aph(atz) |
| 72 | " | (Ipr$_2$)D-Arg | Har(2mpCN) |
| 73 | (5NH$_2$)D-Trp | D-Lys(atz) | Lys(atz) |
| 74 | (6Br)D-Trp | (1For)D-Trp | Arg(bCN) |
| 75 | D-4PAL | D-Aph(iCN) | Aph(iCN) |

Each of the peptides specified in Table V is considered effective to block GnRH-induced LH secretion in vitro at a reasonable concentration. All of the peptides are considered to be effective to prevent ovulation of female mammals at low dosages.

EXAMPLE VI

Peptides as indicated in TABLE VI having the formula:

X—R$_1$—(4F)D—Phe—D—Trp—R$_4$—Glu—R$_6$—Leu—Dbu—Pro—R$_{10}$—NH$_2$ with R$_{11}$ bridging are prepared by the solid-phase procedure referred to above.

TABLE VI

|    | X | $R_1$ | $R_4$ | $R_6$ | $R_{10}$ | $R_{11}$ |
|----|---|-------|-------|-------|----------|----------|
| 76 | Acr | dehydroPro | Asp | D-Lys(atz) | Dpr | Ala |
| 77 | Ac | " | " | D-Aph(hCN) | " | β-Ala |
| 78 | Ac | β-D-2NAL | " | (MeEt)D-Arg | " | Asp |
| 79 | Acr | Pro | " | D-Ser(OtBu) | " | Leu |
| 80 | H | dehydroPro | Abu | (imBzl)D-His | Abu | Val |
| 81 | Bz | (4Br)D-Phe | " | (5Cl)D-Trp | " | Gly |
| 82 | " | D-pGlu | " | (6Br)D-Trp | " | Phe |
| 83 | For | β-D-1NAL | " | D-Dbu(atz) | " | Cys |
| 84 | " | dehydroPro | " | (Ipr$_2$)D-Har | Abu | Orn |
| 85 | Vac | β-D-2NAL | " | D-Pro | " | Lys |
| 86 | " | D-Phe | Asp | D-Ile | Dpr | His |
| 87 | H | dehydroPro | " | D-Aph(chCN) | " | Har |

Each of the peptides listed in Table VI is considered effective to block GnRH-induced LH secretion in vitro at a reasonable concentration. All of the peptides are considered to be effective to prevent ovulation of female mammals at low dosages.

EXAMPLE VII

Peptides as indicated in TABLE VII having the formula:

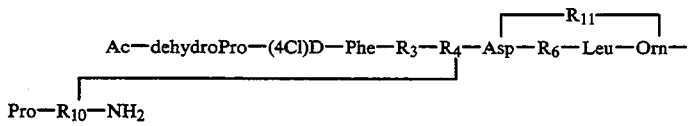

are prepared by the solid-phase procedure referred to above.

TABLE VII

| | R3 | R4 | R6 | R10 | R11 |
|---|---|---|---|---|---|
| 88 | (6NO2)D-Trp | Asp | D-Aph(2mpCN) | Dpr | Phe |
| 89 | " | " | D-Val | " | Dbu |
| 90 | (6F)D-Trp | " | DAph(iCN) | " | Arg |
| 91 | " | " | D-Nva | " | Dpr |
| 92 | (5OCH3)D-Trp | " | D-Har(2mpCN) | " | Val |
| 93 | " | " | D-Dpr(atz) | " | Ala |
| 94 | (1Ac)D-Trp | " | (Me2)D-Har | " | Gly |
| 95 | (1For)D-Trp | " | (5CH2)D-Trp | " | Cys |
| 96 | (6Br)D-Trp | Abu | D-Har(iCN) | Abu | Asp |
| 97 | " | " | D-Leu | Abu | Lys |
| 98 | (6CH3)D-Trp | " | D-Aph(bzCN) | Abu | Glu |
| 99 | (6NH2)D-Trp | Asp | (4NH2)D-Phe | Dpr | Gln |
| 100 | (5NH2)D-Trp | " | D-Ala | " | Asn |

Each of the peptides listed in Table VII is considered effective to block GnRH-induced LH secretion in vitro at a reasonable concentration. All of the peptides are considered to be effective to prevent ovulation of female mammals at low dosages.

EXAMPLE VIII

Peptides as indicated in TABLE VIII having the formula:

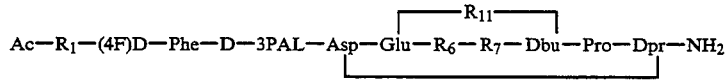

are prepared by the solid phase procedure referred to above.

TABLE VIII

| | R1 | R6 | R7 | R11 |
|---|---|---|---|---|
| 101 | β-D-2NAL | (5NO2)D-Trp | Leu | Cys |
| 102 | " | D-Har(eCN) | " | Har(eCN) |
| 103 | " | D-Har(hCN) | " | Arg(hCN) |
| 104 | " | (EtBu)D-Arg | " | (4gua)Phe |
| 105 | dehydroPro | D-Aph(atz) | 3PAL | (4OCH3)Phe |
| 106 | " | (4NO2)D-Phe | Tyr | Arg(iCN) |
| 107 | β-D-2NAL | D-Dpr(atz) | NML | Aph(atz) |
| 108 | " | β-D-NAL | 4PAL | (gua4CH2)Phe |
| 109 | " | (imBzl)D-His | Leu | Aph(bCN) |
| 110 | " | (6NO2)D-Trp | " | Dpr(atz) |
| 111 | " | D-Tyr | " | Orn(atz) |
| 112 | " | (1For)D-Trp | Phe | Dbu(atz) |
| 113 | " | (6F)D-Trp | NML | Aph(bzCN) |
| 114 | (CαMe/4cl)D-Phe | (4cl)D-Phe | Nle | Orn(atz) |
| 115 | Pro | D-lys(atz) | Met | Lys(atz) |
| 116 | dehydroPro | (6OCH3)D-Trp | Nva | Dbu(atz) |
| 117 | " | (5CH3)D-Trp | " | Dpr |
| 118 | " | (1Ac)D-Trp | (4F)Phe | Aph(iCN) |
| 119 | " | D-Aph(mCN) | NML | Dbu |
| 120 | " | D-Arg(bzCN) | Nle | (4Br)Phe |
| 121 | " | D-Aph(2mpCN) | Trp | Arg(2mpCN) |
| 122 | D-Pro | (2,4Cl2)D-Phe | Nva | Har(bzCN) |
| 123 | β-D-2NAL | D-Aph(atz) | Tyr | Aph(atz) |
| 124 | " | (5Cl)D-Trp | Met | Dpr(atz) |
| 125 | (4Cl)D-Phe | (4Br)D-Phe | 3PAL | Arg (acetate) salt |

Each of the peptides listed in Table VIII is considered effective to block GnRH-induced LH secretion in vitro at a reasonable concentration. All of the peptides are considered to be effective to prevent ovulation of female mammals at low dosages.

EXAMPLE IX

Bicyclic peptides as indicated in TABLE IX having the formula:

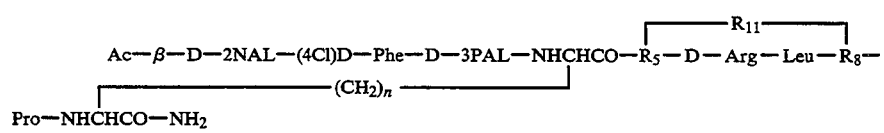

are prepared by the solid-phase procedure referred to above.

TABLE IX

| | n | R5 | R8 | R11 |
|---|---|---|---|---|
| 126 | 5 | Glu | Dbu | Lys |
| 127 | 5 | " | " | Orn |

TABLE IX-continued

|  | n | R$_5$ | R$_8$ | R$_{11}$ |
|---|---|---|---|---|
| 128 | 3 | Hgl | Dpr | (4Cl)Phe |
| 129 | 6 | " | " | Agr(iCN) |
| 130 | 2 | Glu | Dbu | His |
| 131 | 5 | Hgl | Dpr | Dbu(atz) |
| 132 | 3 | " | " | Lys(atz) |
| 133 | 5 | " | Dbu | Arg |
| 134 | 6 | Asp | " | (4NO$_2$)Phe |
| 135 | 2 | Glu | " | (gua4CH$_2$)Phe |
| 136 | 3 | " | Dpr | Orn(atz) |
| 137 | 5 | Hgl | Orn | Lys |
| 138 | 3 | Asp | " | Har(bCN) |

Each of the peptides listed in Table IX is considered effective to block GnRH-induced LH secretion in vitro at a reasonable concentration. All of the peptides are considered to be effective to prevent ovulation of female mammals at low dosages.

The peptides of the invention are often administered in the form of pharmaceutically acceptable, nontoxic salts, or of metal complexes, e.g., with zinc, barium, calcium, magnesium, aluminum or the like (which are considered as addition salts for purposes of this application), or of combinations of the two. Illustrative of such acid addition salts are hydrochloride, hydrobromide, sulphate, phosphate, nitrate, oxalate, fumarate, gluconate, tannate, maleate, acetate, citrate, benzoate, succinate, alginate, malate, ascorbate, tartrate and the like. For example, an aqueous solution of the peptide can be repeatedly treated with in acetic acid and then lyophilized to yield the acetic acid salt thereof. If the active ingredient is to be administered in tablet form, the tablet may contain a pharmaceutically-acceptable diluent or excipient which can include a binder, such as tragacanth, corn starch or gelatin, a disintegrating agent, such as alginic acid, and/or a lubricant, such as magnesium stearate. If administration in liquid form is desired, sweetening and/or flavoring may be used as part of the pharmaceutically-acceptable diluent, and intravenous administration in a carrier such as isotonic saline, phosphate buffer solutions or the like may be effected.

The pharmaceutical compositions will usually contain the peptide in conjunction with a conventional, pharmaceutically-acceptable carrier. Usually, the dosage will be from about 10 micrograms to about 2.5 milligrams of the peptide per kilogram of the body weight of the host when given intravenously; although oral dosages will be higher, it is anticipated that the cyclic nature of these compounds will permit more effective oral administration. Overall, treatment of subjects with these peptides is generally carried out in the same manner as the clinical treatment using other antagonists of GnRH using a suitable liquid carrier in which the peptide is soluble.

It may also be desirable to deliver the GnRH analog over prolonged periods of time, for example, for periods of one week to one year from a single administration, and slow release, depot or implant dosage forms may be utilized. For example, a dosage form may contain a pharmaceutically acceptable non-toxic salt of the compound which has a low degree of solubility in body fluids, for example, an acid addition salt with a polybasic acid, a salt with a polyvalent metal cation, or combination of two such salts. A relatively insoluble salt may also be formulated in a gel, for example, an aluminum stearate gel. A suitable, slow-release depot formulation for injection may also contain the GnRH analog or a salt thereof dispersed or encapsulated in a slow degrading, non-toxic or non-antigenic polymer such as a polylactic acid/polyglycolic acid polymer, for example, as described in U.S. Pat. No. 3,773,919. These compounds may also be formulated into silastic implants.

These peptides can be administered to mammals intravenously, subcutaneously, intramuscularly, orally, percutaneously, e.g. intranasally, or intravaginally to achieve fertility inhibition and/or control and also in applications calling for reversible suppression of gonadal activity, such as for the management of precocious puberty or during radiation- or chemo-therapy. They are also useful for treatment of steroid-dependent tumors. Effective dosages will vary with the form of administration and the particular species of mammal being treated. Certain of these peptides have extremely good solubility characteristics in water and in saline rendering them particularly valuable in this respect. An example of one typical dosage form is a bacteriostatic water solution containing the peptide, which solution is administered to provide a dose in the range of about 0.1 to 2.5 mg/kg of body weight. Oral administration of the peptide may be given in either solid form or liquid form.

Although the invention has been described with regard to its preferred embodiments, it should be understood that changes and modifications as would be obvious to one having the ordinary skill in this art may be made without departing from the scope of the invention which is set forth in the claims which are appended hereto. The art in the design of GnRH antagonists is extremely well developed inasmuch as work has been progressing for some 20 years. Accordingly, although the following three formulae are considered to provide GnRH antagonists having particularly advantageous properties, as should be clear from the foregoing specification and tables, there are equivalent residues that can be substituted for the residues specified in these formulae while retaining comparable biological potency and many of the advantages of the invention. The three formulae are as follows:

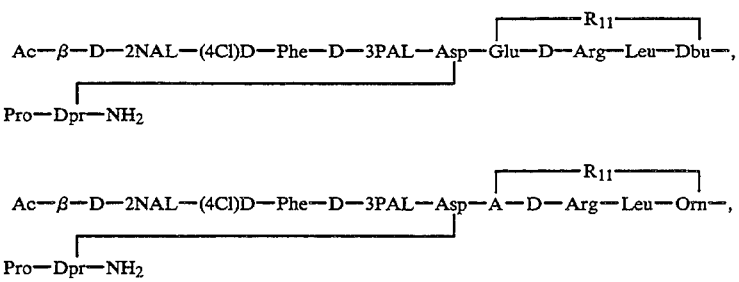

Ac—β—D—2NAL—(4Cl)D—Phe—D—3PAL—Asp—Glu—D—Arg—Leu—Dbu—,
Pro—Dpr—NH$_2$

Ac—β—D—2NAL—(4Cl)D—Phe—D—3PAL—Asp—A—D—Arg—Leu—Orn—,
Pro—Dpr—NH$_2$

-continued and

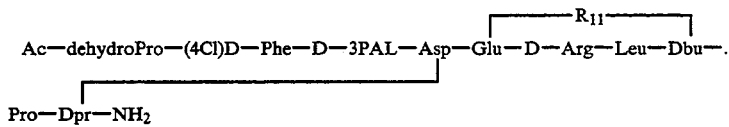

Accordingly, GnRH antagonists having such substitutions are considered to be equivalent. Moreover, in addition to the alternative substituents specifically described herein, there are additional minor adaptations that can be also be made to residues in the various positions of the decapeptides. For example, D-2PAL and D—4PAL are considered to be equivalents of D-3PAL. Substituted Phe, such as (4F)Phe, can be used instead of Phe in the 7-position. Substituted D—Phe, such as (4Cl)D—Phe, and other hydrophobic amino acid residues can also be employed in the 1-position, preferably in D—isomer form, and they are considered equivalents of those specified. Shortened forms of Arg having 1 or 2 less $CH_2$-groups can be employed as a part of the amide cyclizing linkage. Substituted amides can be employed at the C-terminus.

Particular features of the invention are emphasized in the claims which follow.
What is claimed is:

1. A peptide or a nontoxic salt thereof which contains two cyclizing bonds, said peptide having the formula:

Ac-β-D—2NAL—(4Cl)D—Phe—D—3PAL—

—Asp—R₅—D—Arg—Leu—R₈—Pro—Dpr—NH₂ (with R₁₁ cycle)

wherein $R_5$ is Asp or Glu; $R_8$ is Dbu or Orn; $R_{11}$ is Gly, Ala, Sar, β-Ala, NAL, (E)Phe, Arg or His; and E is Cl or H.

2. A method for regulating the secretion of gonadotropins comprising intravenously, subcutaneously, intramuscularly, orally, percutaneously, or intravaginally administering an amount, which is effective to prevent GnRH-induced LH secretion, of a pharmaceutical composition containing a peptide or a nontoxic salt thereof as defined in claim 1 plus a pharmaceutically acceptable carrier so as to provide a daily dosage between about 0.1 and about 2.5 milligrams of said peptide per kilogram of body weight.

3. A peptide according to claim 1 wherein $R_5$ is Glu, $R_8$ is Dbu, and $R_{11}$ is Arg or His.

4. A peptide having the formula:

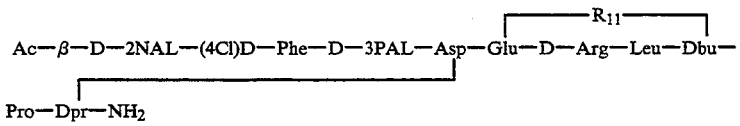

wherein $R_{11}$ is Arg.

5. A peptide according to claim 1 having the formula:

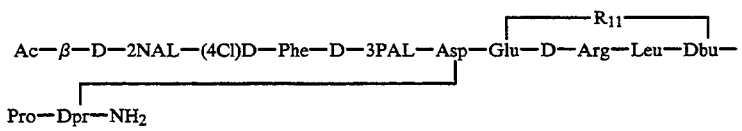

wherein $R_{11}$ is Gly.

6. A peptide according to claim 1 having the formula:

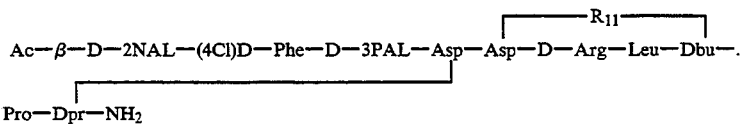

wherein $R_{11}$ is β-Ala.

7. A peptide according to claim 1 having the formula:

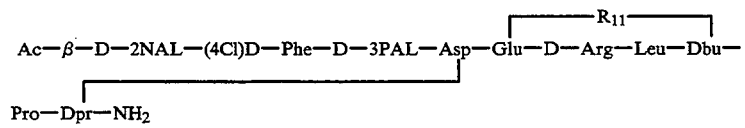

wherein $R_{11}$ is Phe.

8. A peptide according to claim 1 having the formula:

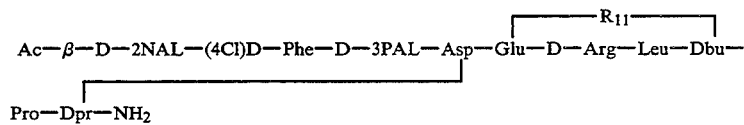
wherein $R_{11}$ is His.
9. A peptide according to claim 1 wherein $R_{11}$ is Arg, Gly, β-Ala, Sar, Phe, β-2NAL, His or (4Cl)Phe.
* * * * *